(12) United States Patent
Jacobsen et al.

(10) Patent No.: US 9,661,996 B2
(45) Date of Patent: May 30, 2017

(54) NEEDLE DELIVERED IMAGING DEVICE

(75) Inventors: Stephen C. Jacobsen, Salt Lake City, UT (US); Fraser M. Smith, Salt Lake City, UT (US)

(73) Assignee: Sarcos LC, Salt Lake City, UT (US)

( * ) Notice: Subject to any disclaimer, the term of this patent is extended or adjusted under 35 U.S.C. 154(b) by 0 days.

(21) Appl. No.: 12/896,731

(22) Filed: Oct. 1, 2010

(65) Prior Publication Data
US 2011/0245605 A1  Oct. 6, 2011

Related U.S. Application Data

(60) Provisional application No. 61/247,890, filed on Oct. 1, 2009.

(51) Int. Cl.
| | |
|---|---|
| *A61B 1/04* | (2006.01) |
| *A61B 1/00* | (2006.01) |
| *A61B 1/05* | (2006.01) |
| *A61B 1/015* | (2006.01) |
| *A61B 1/018* | (2006.01) |
| *A61B 1/313* | (2006.01) |
| *A61B 10/02* | (2006.01) |
| A61B 17/34 | (2006.01) |
| A61B 90/00 | (2016.01) |

(52) U.S. Cl.
CPC .............. *A61B 1/05* (2013.01); *A61B 1/015* (2013.01); *A61B 1/018* (2013.01); *A61B 1/313* (2013.01); *A61B 10/0283* (2013.01); *A61B 17/3421* (2013.01); *A61B 90/361* (2016.02)

(58) Field of Classification Search
None
See application file for complete search history.

(56) References Cited

U.S. PATENT DOCUMENTS

| 3,787,121 A | 1/1974 | Lowy et al. |
|---|---|---|
| 3,817,635 A | 6/1974 | Kawahar |
| 3,856,000 A | 12/1974 | Chikama |

(Continued)

FOREIGN PATENT DOCUMENTS

| CN | 1481753 | 3/2004 |
|---|---|---|
| DE | 197 42 973 | 4/1998 |

(Continued)

OTHER PUBLICATIONS

PCT Application PCT/US2010/051188; filed Oct. 1, 2010; Stephen C. Jacobsen; International Search Report mailed Jul. 13, 2011.

(Continued)

*Primary Examiner* — Alexandra Newton
(74) *Attorney, Agent, or Firm* — Thorpe North & Western LLP

(57) ABSTRACT

A hollow elongated cylinder is disclosed having a distal end and a proximal end, the proximal end configured to be removably connectable to a distal end of a syringe. An umbilical is removably inserted within said cylinder and configured for detachable connection to a data processor and a display device having a solid state imaging device disposed on a distal end of the umbilical. A lens system is disposed on a distal end of the solid state imaging device. The umbilical is inserted within the cylinder such that the distal end of the lens system is disposed at approximately the distal end of the cylinder.

17 Claims, 6 Drawing Sheets

(56) References Cited

U.S. PATENT DOCUMENTS

| | | |
|---|---|---|
| 3,886,933 A | 6/1975 | Mori et al. |
| 3,918,438 A | 11/1975 | Hayamizu et al. |
| 3,971,065 A | 7/1976 | Bayer |
| 4,277,168 A | 7/1981 | Oku |
| 4,283,115 A | 8/1981 | Fraissl |
| 4,403,985 A | 9/1983 | Boretos |
| 4,475,902 A | 10/1984 | Schubert |
| 4,487,206 A | 12/1984 | Aagard |
| 4,491,865 A | 1/1985 | Danna et al. |
| 4,515,444 A | 5/1985 | Prescott et al. |
| 4,573,450 A | 3/1986 | Arakawa |
| 4,585,349 A | 4/1986 | Gross et al. |
| 4,588,294 A | 5/1986 | Siegmund |
| 4,589,404 A | 5/1986 | Barath et al. |
| 4,593,313 A | 6/1986 | Nagasaki et al. |
| 4,594,605 A | 6/1986 | Kramer |
| 4,594,613 A | 6/1986 | Shinbori et al. |
| 4,600,831 A | 7/1986 | Hutley |
| 4,604,992 A | 8/1986 | Sato |
| 4,620,534 A | 11/1986 | Zartman |
| 4,621,284 A | 11/1986 | Nishioka et al. |
| 4,622,954 A | 11/1986 | Arakawa et al. |
| 4,626,079 A | 12/1986 | Nakamura et al. |
| 4,641,927 A | 2/1987 | Prescott et al. |
| 4,646,724 A | 3/1987 | Sato et al. |
| 4,672,218 A | 6/1987 | Chrisman et al. |
| 4,706,118 A | 11/1987 | Kato et al. |
| 4,707,134 A | 11/1987 | McLachlan et al. |
| 4,723,843 A | 2/1988 | Zobel |
| 4,725,721 A | 2/1988 | Nakamura |
| 4,745,470 A | 5/1988 | Yabe et al. |
| 4,745,471 A | 5/1988 | Takamura et al. |
| 4,783,591 A | 11/1988 | Sullivan |
| 4,785,815 A | 11/1988 | Cohen |
| 4,790,624 A | 12/1988 | Van Hoye et al. |
| 4,791,479 A | 12/1988 | Ogiu et al. |
| 4,802,487 A | 2/1989 | Martin et al. |
| 4,803,562 A | 2/1989 | Eino |
| 4,832,003 A | 5/1989 | Yabe |
| 4,843,416 A | 6/1989 | Brower |
| 4,846,785 A | 7/1989 | Cassou et al. |
| 4,859,040 A | 8/1989 | Kitagishi et al. |
| 4,867,137 A | 9/1989 | Takahashi |
| 4,867,138 A | 9/1989 | Kubota et al. |
| 4,867,174 A | 9/1989 | Skribiski |
| 4,880,298 A | 11/1989 | Takada |
| 4,895,138 A | 1/1990 | Yabe |
| 4,916,534 A | 4/1990 | Takhashi et al. |
| 4,926,257 A | 5/1990 | Miyazaki |
| 4,930,880 A | 6/1990 | Miyauchi |
| 4,932,394 A | 6/1990 | Nanaumi |
| 4,934,340 A | 6/1990 | Ebling et al. |
| 4,941,457 A | 7/1990 | Hasegawa |
| 4,998,807 A | 3/1991 | Uzawa et al. |
| 5,006,928 A | 4/1991 | Kawajiri et al. |
| 5,009,483 A | 4/1991 | Rockwell, III |
| 5,021,888 A | 6/1991 | Kondou et al. |
| 5,032,913 A | 7/1991 | Hattori et al. |
| 5,040,069 A | 8/1991 | Matsumoto et al. |
| 5,061,036 A | 10/1991 | Gordon |
| 5,093,719 A | 3/1992 | Prescott |
| 5,105,269 A | 4/1992 | Nakamura et al. |
| 5,106,387 A | 4/1992 | Kittrell et al. |
| 5,109,859 A | 5/1992 | Jenkins |
| 5,111,804 A | 5/1992 | Funakoshi |
| 5,113,254 A | 5/1992 | Kanno et al. |
| 5,121,213 A | 6/1992 | Nishioka |
| 5,126,639 A | 6/1992 | Srivastava |
| 5,130,804 A | 7/1992 | Tamura et al. |
| 5,152,277 A | 10/1992 | Honda et al. |
| 5,165,063 A | 11/1992 | Strater et al. |
| 5,166,656 A | 11/1992 | Badehi et al. |
| 5,182,672 A | 1/1993 | Mukai et al. |
| 5,188,093 A * | 2/1993 | Lafferty et al. ............ 600/109 |
| 5,190,523 A * | 3/1993 | Lindmayer .................... 604/72 |
| 5,191,203 A | 3/1993 | McKinley |
| 5,198,894 A | 3/1993 | Hicks |
| 5,209,219 A * | 5/1993 | Hollobaugh ................ 600/154 |
| 5,220,198 A | 6/1993 | Tsuji |
| 5,222,477 A | 6/1993 | Lia |
| 5,228,430 A | 7/1993 | Sakamoto |
| 5,258,834 A | 11/1993 | Tsuji et al. |
| 5,289,434 A | 2/1994 | Berni |
| 5,290,555 A | 3/1994 | Guthauser et al. |
| 5,291,010 A | 3/1994 | Tsuji |
| 5,298,741 A | 3/1994 | Walt et al. |
| 5,304,173 A | 4/1994 | Kittrell et al. |
| 5,305,098 A | 4/1994 | Matsunaka et al. |
| 5,318,024 A | 6/1994 | Kittrell et al. |
| 5,361,166 A | 11/1994 | Atkinson et al. |
| 5,365,268 A | 11/1994 | Minami |
| 5,376,960 A | 12/1994 | Wurster |
| 5,377,047 A | 12/1994 | Broome et al. |
| 5,381,784 A | 1/1995 | Adair |
| 5,396,366 A | 3/1995 | Brown et al. |
| 5,398,685 A | 3/1995 | Wilk et al. |
| 5,402,769 A | 4/1995 | Tsuji |
| 5,406,940 A * | 4/1995 | Melzer ............... A61B 1/00087 600/106 |
| 5,408,999 A | 4/1995 | Singh et al. |
| 5,430,475 A | 7/1995 | Goto et al. |
| 5,434,615 A | 7/1995 | Matumoto |
| 5,436,655 A | 7/1995 | Hiyama et al. |
| 5,438,975 A | 8/1995 | Miyagi et al. |
| 5,440,669 A | 8/1995 | Rakuljie et al. |
| 5,450,243 A | 9/1995 | Nishioka |
| 5,455,455 A | 10/1995 | Badehi |
| 5,458,612 A | 10/1995 | Chin |
| 5,459,570 A | 10/1995 | Swanson et al. |
| 5,469,841 A | 11/1995 | Kobayashi et al. |
| 5,494,483 A | 2/1996 | Adair |
| 5,512,940 A | 4/1996 | Takasugi et al. |
| 5,517,997 A | 5/1996 | Fontenot |
| 5,531,664 A | 7/1996 | Adachi et al. |
| 5,547,455 A | 8/1996 | McKenna et al. |
| 5,547,906 A | 8/1996 | Badehi |
| 5,594,497 A | 1/1997 | Ahern |
| 5,603,687 A | 2/1997 | Hori et al. |
| 5,607,435 A | 3/1997 | Sachdeva et al. |
| 5,621,574 A | 4/1997 | Foo |
| 5,630,788 A | 5/1997 | Forkner et al. |
| 5,647,368 A | 7/1997 | Zeng et al. |
| 5,662,621 A | 9/1997 | Lafontaine |
| 5,673,083 A | 9/1997 | Izumi et al. |
| 5,685,311 A | 11/1997 | Hara |
| 5,693,043 A | 12/1997 | Kittrell et al. |
| 5,704,892 A | 1/1998 | Adair |
| 5,716,323 A | 2/1998 | Lee |
| 5,716,759 A | 2/1998 | Badehi |
| 5,722,403 A | 3/1998 | McGee et al. |
| 5,732,150 A | 3/1998 | Zhou et al. |
| 5,740,808 A | 4/1998 | Panescu et al. |
| 5,749,827 A | 5/1998 | Minami |
| 5,751,340 A | 5/1998 | Strobl et al. |
| 5,752,518 A | 5/1998 | McGee et al. |
| 5,769,792 A | 6/1998 | Palcic et al. |
| 5,772,597 A | 6/1998 | Goldberger et al. |
| 5,776,049 A | 7/1998 | Takahashi |
| 5,783,829 A | 7/1998 | Sealock et al. |
| 5,784,098 A | 7/1998 | Shoji et al. |
| 5,792,984 A | 8/1998 | Bloom |
| 5,800,341 A | 9/1998 | McKenna et al. |
| 5,807,261 A | 9/1998 | Benaron et al. |
| 5,808,665 A | 9/1998 | Green |
| 5,818,644 A | 10/1998 | Noda |
| 5,827,172 A | 10/1998 | Takahashi et al. |
| 5,840,017 A | 11/1998 | Furusawa et al. |
| 5,846,185 A | 12/1998 | Carollo |
| 5,848,969 A | 12/1998 | Panescu et al. |
| 5,865,729 A | 2/1999 | Meehan et al. |
| 5,870,229 A | 2/1999 | Tsuchuda |
| 5,873,816 A | 2/1999 | Kagawa et al. |
| 5,879,285 A | 3/1999 | Ishii |
| 5,904,651 A | 5/1999 | Swanson et al. |

(56) References Cited

U.S. PATENT DOCUMENTS

| | | |
|---|---|---|
| 5,908,445 A | 6/1999 | Whayne et al. |
| 5,913,817 A | 6/1999 | Lee |
| 5,916,155 A | 6/1999 | Levinson et al. |
| 5,929,900 A | 7/1999 | Yamanaka et al. |
| 5,940,126 A | 8/1999 | Kimura |
| 5,947,894 A | 9/1999 | Chapman et al. |
| 5,951,462 A | 9/1999 | Yamanaka |
| 5,957,849 A | 9/1999 | Munro |
| 5,971,915 A | 10/1999 | Yamamoto et al. |
| 5,973,779 A | 10/1999 | Ansari et al. |
| 5,980,663 A | 11/1999 | Badehi |
| 5,989,185 A | 11/1999 | Miyazaki |
| 5,998,878 A | 12/1999 | Johnson |
| 5,999,327 A | 12/1999 | Nagaoka |
| 6,007,483 A * | 12/1999 | Kieturakis ......... A61B 17/0218 600/115 |
| 6,008,123 A | 12/1999 | Kook et al. |
| 6,014,919 A | 1/2000 | Jacobsen et al. |
| 6,022,758 A | 2/2000 | Badehi |
| 6,040,235 A | 3/2000 | Badehi |
| 6,059,760 A | 5/2000 | Sandmore et al. |
| 6,095,970 A | 8/2000 | Hidaka et al. |
| 6,117,707 A | 9/2000 | Badehi |
| 6,118,476 A | 9/2000 | Morito et al. |
| 6,133,637 A | 10/2000 | Hikita et al. |
| 6,134,003 A | 10/2000 | Terney et al. |
| 6,139,489 A | 10/2000 | Wampler et al. |
| 6,142,930 A | 11/2000 | Ito et al. |
| 6,161,035 A | 12/2000 | Furusawa |
| 6,184,923 B1 | 2/2001 | Miyazaki |
| 6,193,685 B1 | 2/2001 | Goodin |
| 6,211,955 B1 | 4/2001 | Basiji et al. |
| 6,224,969 B1 | 5/2001 | Steenbergen et al. |
| 6,247,928 B1 * | 6/2001 | Meller ............... A61B 17/1637 433/165 |
| 6,261,226 B1 | 7/2001 | McKenna et al. |
| 6,262,855 B1 | 7/2001 | Greisz |
| 6,280,960 B1 | 8/2001 | Carr |
| 6,288,172 B1 | 9/2001 | Goetz et al. |
| 6,319,745 B1 | 11/2001 | Bertin et al. |
| 6,322,498 B1 | 11/2001 | Gravenstein et al. |
| 6,327,096 B1 | 12/2001 | Tsuchida |
| 6,352,503 B1 | 3/2002 | Matsue |
| 6,361,491 B1 | 3/2002 | Hasegawa et al. |
| 6,366,726 B1 | 4/2002 | Wach et al. |
| 6,375,635 B1 | 4/2002 | Moutafis et al. |
| 6,384,397 B1 | 5/2002 | Takiar et al. |
| 6,384,884 B1 | 5/2002 | Nakamura et al. |
| 6,396,116 B1 | 5/2002 | Kelly et al. |
| 6,407,768 B1 | 6/2002 | Ishikaw |
| 6,445,939 B1 | 9/2002 | Swanson et al. |
| 6,456,423 B1 | 9/2002 | Nayfeh et al. |
| 6,471,636 B1 | 10/2002 | Sano et al. |
| 6,485,413 B1 | 11/2002 | Boppart et al. |
| 6,522,913 B2 | 2/2003 | Swanson et al. |
| 6,533,722 B2 | 3/2003 | Nakashima |
| 6,537,205 B1 | 3/2003 | Smith |
| 6,551,302 B1 | 4/2003 | Rosinko et al. |
| 6,552,796 B2 | 4/2003 | Magnin et al. |
| 6,561,972 B2 | 5/2003 | Ooshima et al. |
| 6,570,659 B2 | 5/2003 | Schmitt |
| 6,573,950 B1 | 6/2003 | Hirata et al. |
| 6,585,717 B1 | 7/2003 | Wittenberg et al. |
| 6,595,913 B2 | 7/2003 | Takahashi |
| 6,618,614 B1 | 9/2003 | Chance et al. |
| 6,622,367 B1 | 9/2003 | Bolduc et al. |
| 6,643,071 B2 | 11/2003 | Schnitzer |
| 6,658,279 B2 | 12/2003 | Swanson et al. |
| 6,659,941 B2 | 12/2003 | Weber et al. |
| 6,695,787 B2 | 2/2004 | Hogendijk et al. |
| 6,710,919 B1 | 3/2004 | Clausen |
| 6,719,686 B2 | 4/2004 | Coakley et al. |
| 6,727,313 B2 | 4/2004 | Zhou et al. |
| 6,756,437 B1 | 6/2004 | Xue et al. |
| 6,761,684 B1 | 7/2004 | Speirer |
| 6,785,048 B2 | 8/2004 | Yamaguchi et al. |
| 6,826,422 B1 | 11/2004 | Modell et al. |
| 6,827,683 B2 | 12/2004 | Otawara |
| 6,833,916 B2 | 12/2004 | Osipchuk et al. |
| 6,834,158 B1 | 12/2004 | Templeton |
| 6,842,288 B1 | 1/2005 | Liu et al. |
| 6,850,659 B2 | 2/2005 | Han |
| 6,879,851 B2 | 4/2005 | McNamara et al. |
| 6,881,448 B1 | 4/2005 | Hattori |
| 6,891,984 B2 | 5/2005 | Petersen et al. |
| 6,893,432 B2 | 5/2005 | Intintoli et al. |
| 6,894,729 B2 | 5/2005 | Hirata et al. |
| 6,898,458 B2 | 5/2005 | Zeng et al. |
| 6,900,913 B2 | 5/2005 | Chen |
| 6,930,705 B2 | 8/2005 | Tanaka |
| 6,937,268 B2 | 8/2005 | Ogawa |
| 6,939,348 B2 | 9/2005 | Malecki et al. |
| 6,941,041 B2 | 9/2005 | Yamaguchi et al. |
| 6,944,204 B2 | 9/2005 | Zhou et al. |
| 6,953,432 B2 | 10/2005 | Schiefer |
| 6,956,624 B2 | 10/2005 | Hirata et al. |
| 6,960,165 B2 | 11/2005 | Ueno et al. |
| 6,982,740 B2 | 1/2006 | Adair et al. |
| 6,990,271 B2 | 1/2006 | Gafsi et al. |
| 7,030,904 B2 | 4/2006 | Adair et al. |
| 7,033,317 B2 | 4/2006 | Pruitt |
| 7,058,294 B2 | 6/2006 | Nakahara |
| 7,075,576 B2 | 7/2006 | Creasey et al. |
| 7,081,927 B2 | 7/2006 | Hirata et al. |
| 7,091,500 B2 | 8/2006 | Schnitzer |
| 7,098,871 B1 | 8/2006 | Tegreene et al. |
| 7,102,817 B1 | 9/2006 | Wu |
| 7,108,657 B2 | 9/2006 | Irion et al. |
| 7,153,299 B1 | 12/2006 | Tu et al. |
| 7,165,552 B2 | 1/2007 | Deem et al. |
| 7,166,537 B2 | 1/2007 | Jacobsen et al. |
| 7,167,317 B2 | 1/2007 | Jung et al. |
| 7,186,251 B2 | 3/2007 | Malecki et al. |
| 7,218,822 B2 | 5/2007 | Treado et al. |
| 7,221,388 B2 | 5/2007 | Sudo et al. |
| 7,234,816 B2 | 6/2007 | Bruzzone et al. |
| 7,304,310 B1 | 12/2007 | Shortt et al. |
| 7,393,321 B2 | 7/2008 | Doguchi et al. |
| 7,420,675 B2 | 9/2008 | Giakos |
| 7,433,552 B2 | 10/2008 | Kiesel et al. |
| 7,511,891 B2 | 3/2009 | Messerschmidt |
| 7,554,597 B2 | 6/2009 | Scherling |
| 7,591,780 B2 | 9/2009 | Jacobsen |
| 7,629,659 B2 | 12/2009 | Jacobsen |
| 7,787,939 B2 | 8/2010 | Jacobsen et al. |
| 7,823,215 B2 | 10/2010 | Giakos |
| 7,835,074 B2 | 11/2010 | Jacobsen et al. |
| 7,842,046 B1 | 11/2010 | Nakao |
| 7,901,870 B1 | 3/2011 | Wach |
| 8,183,057 B2 | 5/2012 | Isojima |
| 8,326,389 B2 | 12/2012 | Epstein |
| 8,838,195 B2 | 9/2014 | Markle |
| 2001/0007051 A1 | 7/2001 | Nakashima |
| 2001/0007511 A1 | 7/2001 | Minami et al. |
| 2001/0012053 A1 | 8/2001 | Nakamura |
| 2001/0024848 A1 | 9/2001 | Nakamura |
| 2001/0049509 A1 | 12/2001 | Sekine et al. |
| 2002/0007110 A1 | 1/2002 | Irion |
| 2002/0080248 A1 | 6/2002 | Adair et al. |
| 2002/0109774 A1 | 8/2002 | Meron et al. |
| 2002/0111534 A1 | 8/2002 | Suzuki et al. |
| 2002/0166946 A1 | 11/2002 | Iizuka et al. |
| 2002/0188204 A1 | 12/2002 | McNamara |
| 2002/0193660 A1 | 12/2002 | Weber |
| 2003/0071342 A1 | 4/2003 | Honda et al. |
| 2003/0092995 A1 | 5/2003 | Thompson |
| 2003/0114732 A1 | 6/2003 | Webler et al. |
| 2003/0171666 A1 | 9/2003 | Loeb |
| 2003/0197812 A1 | 10/2003 | Hirata et al. |
| 2003/0199761 A1 | 10/2003 | Yock |
| 2003/0202127 A1 | 10/2003 | Hirata et al. |
| 2003/0208211 A1 | 11/2003 | Kortenbach |
| 2003/0220574 A1 * | 11/2003 | Markus et al. ............... 600/466 |
| 2003/0222325 A1 | 12/2003 | Jacobsen |

(56) References Cited

U.S. PATENT DOCUMENTS

| | | |
|---|---|---|
| 2004/0006274 A1 | 1/2004 | Giller et al. |
| 2004/0015049 A1 | 1/2004 | Zaar |
| 2004/0017961 A1 | 1/2004 | Petersen et al. |
| 2004/0059204 A1 | 3/2004 | Marshall |
| 2004/0070134 A1 | 4/2004 | Eskey |
| 2004/0097788 A1 | 5/2004 | Mourlas et al. |
| 2004/0097804 A1 | 5/2004 | Sobe |
| 2004/0111031 A1 | 6/2004 | Alfano et al. |
| 2004/0115955 A1 | 6/2004 | Motoyama et al. |
| 2004/0165858 A1 | 8/2004 | Curatolo |
| 2004/0181148 A1 | 9/2004 | Uchiyama et al. |
| 2004/0222031 A1 | 11/2004 | Szalony et al. |
| 2004/0225222 A1 | 11/2004 | Zeng et al. |
| 2004/0260148 A1 | 12/2004 | Schnitzer |
| 2005/0004453 A1* | 1/2005 | Tearney ............... A61B 5/0066 600/427 |
| 2005/0054902 A1 | 3/2005 | Konno |
| 2005/0065504 A1 | 3/2005 | Melsky et al. |
| 2005/0084229 A1 | 4/2005 | Babbitt et al. |
| 2005/0088576 A1 | 4/2005 | Hirata et al. |
| 2005/0099824 A1 | 5/2005 | Dowling et al. |
| 2005/0110892 A1 | 5/2005 | Yun |
| 2005/0124875 A1 | 6/2005 | Kawano et al. |
| 2005/0152421 A1 | 7/2005 | Fujitani |
| 2005/0154277 A1 | 7/2005 | Tang et al. |
| 2005/0158899 A1 | 7/2005 | Jacobsen et al. |
| 2005/0171521 A1 | 8/2005 | Brucker et al. |
| 2005/0174649 A1 | 8/2005 | Okada et al. |
| 2005/0187568 A1 | 8/2005 | Klenk et al. |
| 2005/0197534 A1 | 9/2005 | Barbato et al. |
| 2005/0231718 A1 | 10/2005 | Goodall et al. |
| 2005/0234345 A1 | 10/2005 | Yang |
| 2005/0264813 A1 | 12/2005 | Giakos |
| 2005/0267340 A1 | 12/2005 | Ishihara et al. |
| 2005/0288555 A1 | 12/2005 | Binmoeller |
| 2006/0009682 A1 | 1/2006 | Nagasawa et al. |
| 2006/0013593 A1 | 1/2006 | Yokoo et al. |
| 2006/0017928 A1 | 1/2006 | Crowther |
| 2006/0051036 A1 | 3/2006 | Treado |
| 2006/0069312 A1 | 3/2006 | O.Connor |
| 2006/0079835 A1 | 4/2006 | Frassica |
| 2006/0106283 A1 | 5/2006 | Wallace et al. |
| 2006/0142700 A1* | 6/2006 | Sobelman et al. ....... 604/167.04 |
| 2006/0146172 A1 | 7/2006 | Jacobsen et al. |
| 2006/0161048 A1 | 7/2006 | Squicciarini |
| 2006/0181774 A1 | 8/2006 | Ojima et al. |
| 2006/0252994 A1 | 11/2006 | Ratnakar |
| 2006/0253088 A1 | 11/2006 | Chow et al. |
| 2007/0010709 A1 | 1/2007 | Reinschke |
| 2007/0032796 A1 | 2/2007 | Chin-Chen et al. |
| 2007/0066869 A1 | 3/2007 | Hoffman |
| 2007/0073321 A1 | 3/2007 | Mikkaichi et al. |
| 2007/0083232 A1 | 4/2007 | Lee |
| 2007/0088276 A1 | 4/2007 | Stubbs et al. |
| 2007/0135803 A1 | 6/2007 | Belson |
| 2007/0146887 A1 | 6/2007 | Ikeda et al. |
| 2007/0208252 A1 | 9/2007 | Makower |
| 2007/0228300 A1 | 10/2007 | Smith |
| 2007/0233187 A1 | 10/2007 | Lobello |
| 2007/0239066 A1 | 10/2007 | Laham et al. |
| 2007/0255392 A1 | 11/2007 | Johnson |
| 2007/0293727 A1 | 12/2007 | Goldfarb et al. |
| 2008/0045794 A1 | 2/2008 | Belson |
| 2008/0058601 A1 | 3/2008 | Fujimori |
| 2008/0071141 A1 | 3/2008 | Gattani et al. |
| 2008/0094326 A1 | 4/2008 | Yamaki et al. |
| 2008/0114309 A1* | 5/2008 | Zuckerman ................... 604/264 |
| 2008/0143822 A1 | 6/2008 | Wang et al. |
| 2008/0160257 A1 | 7/2008 | Takada et al. |
| 2008/0177141 A1 | 7/2008 | Wu et al. |
| 2008/0183080 A1 | 7/2008 | Abraham |
| 2008/0188767 A1 | 8/2008 | Oaki et al. |
| 2008/0227893 A1 | 9/2008 | Tamori et al. |
| 2008/0267562 A1 | 10/2008 | Wang et al. |
| 2009/0027765 A1 | 1/2009 | Kamijima |
| 2009/0036764 A1 | 2/2009 | Rivas et al. |
| 2009/0054791 A1 | 2/2009 | Flusberg |
| 2009/0082626 A1 | 3/2009 | Ichimura et al. |
| 2009/0119808 A1 | 5/2009 | Giakos |
| 2009/0137928 A1 | 5/2009 | Quick et al. |
| 2009/0143645 A1 | 6/2009 | Matthes |
| 2009/0156899 A1 | 6/2009 | Konishi |
| 2009/0180197 A1 | 7/2009 | Jacobsen |
| 2009/0213894 A1 | 8/2009 | Grapov et al. |
| 2009/0234325 A1 | 9/2009 | Rozenberg et al. |
| 2009/0287048 A1 | 11/2009 | Jacobson et al. |
| 2009/0306474 A1 | 12/2009 | Wilson |
| 2010/0016662 A1 | 1/2010 | Salsman et al. |
| 2010/0085567 A1 | 4/2010 | Dottery et al. |
| 2010/0106134 A1* | 4/2010 | Jolly et al. ................... 604/506 |
| 2010/0134872 A1 | 6/2010 | Johnson et al. |
| 2010/0171821 A1 | 7/2010 | Jacobsen et al. |
| 2010/0248178 A1 | 9/2010 | Nahlieli |
| 2011/0204265 A1 | 8/2011 | Smith et al. |

FOREIGN PATENT DOCUMENTS

| | | |
|---|---|---|
| DE | 19859434 | 7/2000 |
| EP | 0482997 | 4/1992 |
| EP | 0550 995 | 7/1993 |
| EP | 0639043 | 2/1995 |
| EP | 0681809 | 11/1995 |
| EP | 1104182 | 5/2001 |
| EP | 1195130 | 4/2002 |
| EP | 1477104 | 11/2004 |
| EP | 1488737 | 12/2004 |
| EP | 1626436 | 2/2006 |
| EP | 1647569 | 4/2006 |
| EP | 1880656 | 1/2008 |
| JP | 58-046924 | 3/1983 |
| JP | S61-261713 | 11/1986 |
| JP | 63-155115 | 6/1988 |
| JP | H01-282514 | 11/1989 |
| JP | H05-039501 | 2/1993 |
| JP | 5 -049602 | 3/1993 |
| JP | H05-197828 | 8/1993 |
| JP | H07-148105 | 6/1995 |
| JP | H07-222712 | 8/1995 |
| JP | 08-076028 | 3/1996 |
| JP | 08084700 | 4/1996 |
| JP | H09-021963 | 1/1997 |
| JP | 11 137512 | 5/1999 |
| JP | 2001/314365 | 11/2001 |
| JP | 2004-004929 | 1/2004 |
| JP | 2004-086553 | 3/2004 |
| JP | 2004-094873 | 3/2004 |
| JP | 2004/329700 | 11/2004 |
| JP | 2005334462 | 8/2005 |
| JP | 2006/162418 | 6/2006 |
| JP | 2006/320369 | 11/2006 |
| JP | 2007-167387 | 7/2007 |
| JP | 2007/312290 | 11/2007 |
| JP | 2009/067946 | 4/2009 |
| KR | 10-20080027935 | 3/2008 |
| WO | WO 98/38907 | 9/1998 |
| WO | WO 99/40624 | 8/1999 |
| WO | WO 00/54033 | 9/2000 |
| WO | WO 03/081831 | 10/2003 |
| WO | WO 2006/060777 | 6/2006 |
| WO | WO 2007/138889 | 12/2007 |

OTHER PUBLICATIONS

Xie et al; GRIN Lens Rod Based Probe for Endoscopic Spectral Domain Optical Coherence Tomography with Fast Dynamic Focus Tracking; Optics Express; Apr. 17, 2006; 9 pages; vol. 14, No. 8.
Xuting Technologies Co., Ltd.; http://www.xutingby.com/en/products/glinfo.htm; as accessed May 1, 2008; 5 pages.
Frequency; Wikipedia, The Free Encyclopedia; http://en.wikipedia.org/wiki/Frequency; as accessed May 9, 2008; 4 pages.
Introduction to Gradient Index Optics; http://grintech.de/e_main_grin.htm; as accessed May 1, 2008; 7 pages.

(56) References Cited

OTHER PUBLICATIONS

Gradient Index (GRIN) Lenses; Grin Tech; 2 pages; The Applicant believes the year of publication of this article is prior to the effective US filing date of this patent application.

Shape Memory Polymers—Biodegradable Sutures; http://www.azom.com/details.asp?ArticleID=1542; as accessed Nov. 6, 2007; 4 pages.

Surgical Needles for Use With Sutures; Wikipedia, The Free Encyclopedia; as accessed Nov. 6, 2007; 6 pages.

Harder et al; Against the Migraine; Science News Online; http://www.sciencenews.org/articles/20050219/bob8.asp; Feb. 19, 2005; 11 pages.

U.S. Appl. No. 12/152,730; filed May 16, 2008; Stephen C. Jacobson; office action issued Sep. 16, 2011.

Boppart, S.A. et al., "Forward-imaging instruments for optical coherence tomography." Optics Letters, Nov. 1, 1997, vol. 22, No. 21, pp. 1618-1620.

Boppart, S.A. et al., "Optical imaging technology in minimally invasive surgery," Surg. Endosc., 1999, vol. 13, pp. 718-722.

Fujimoto, JG et al., "High resolution in vivo intra-arterial imaging with optical coherence tomography," Heart, 1999, vol. 82, pp. 128-133.

Hirofumi Tsuchida et al., "Design of imaging lens systems that use low dispersive radial gradient-index rod," Jpn, J. Appl. Phys. vol. 37 No. 6B, Jun. 30, 1998, pp. 3633-3637.

http://news.thomasnet.com/fullstory/23462 "Near-IR Camera Utilizes CCD Array with Phosphor Coating"; Jun. 11, 2003; 5 pages.

J. Knittel et al., "Endoscope-compatible confocal microscope using a gradient index-lens system" Optics Communications, vol. 188, Issue 5-6, Feb. 2001, pp. 267-273.

Jacobsen, Stephen C., U.S. Appl. No. 10/391,489, filed Mar. 17, 2003.

Jacobsen, Stephen C., U.S. Appl. No. 10/391,490, filed Mar. 17, 2003.

Jacobsen, Stephen C., U.S. Appl. No. 10/391,513, filed Mar. 17, 2003.

Jacobsen, Stephen C., U.S. Appl. No. 11/292,902, filed Dec. 1, 2005.

Jacobsen, Stephen C., U.S. Appl. No. 11/810,702, filed Jun. 5, 2007.

Jacobsen, Stephen C., U.S. Appl. No. 12/008,486, filed Jan. 11, 2008.

Jacobsen, Stephen C., U.S. Appl. No. 12/079,741, filed Mar. 27, 2008.

Jacobsen, Stephen C., U.S. Appl. No. 12/152,730, filed May 16, 2008.

Jacobsen, Stephen C., U.S. Appl. No. 12/487,481, filed Jun. 18, 2009.

Jacobsen, Stephen C., U.S. Appl. No. 12/487,495, filed Jun. 18, 2009.

Jacobsen, Stephen C., U.S. Appl. No. 12/512,188, filed Jul. 30, 2009.

Jacobsen, Stephen C.; U.S. Appl. No. 12/611,776; filed Nov. 3, 2009.

Jacobsen, Stephen C.; U.S. Appl. No. 12/792,562; filed Jun. 2, 2010.

Jacobsen, Stephen C.; U.S. Appl. No. 12/896,731; filed Oct. 1, 2010.

Jacobsen, Stephen C.; U.S. Appl. No. 12/896,732; filed Oct. 1, 2010.

Jacobsen, Stephen C.; U.S. Appl. No. 12/896,737; filed Oct. 1, 2010.

Jacobsen, Stephen C.; U.S. Appl. No. 12/896,743; filed Oct. 1, 2010.

Jacobsen, Stephen C.; U.S. Appl. No. 12/938,672; filed Nov. 3, 2010.

Jacobsen, Stephen C.; U.S. Appl. No. 12/946,442; filed Nov. 15, 2010.

Johansson et al.; "Generation of Turquoise Light by Sum Frequency Mixing of a Diode-Pumped Solid-State Laser and a Laser Diode in Periodically Poled KTP," Optics Express; Oct. 4, 2004; pp. 4935-4940; vol. 12, No. 12.

Literature from GRIN TECH, "In vivo medical confocal imaging and optical coherence tomography," www.grintech.de, Revision Jun. 2001, pp. 1-3.

Microcam, Minast Project 5.04, Nov. 11, 1999, http://www.imt.unine.ch/ESPLAB/www/projects/Microcam/, pp. 1-16.

Nguyen, Clark, "Communications Applications of Microelectromechanical Systems," Proceedings, Sensors Expo, May 19-21, 1998, San Jose, CA. pp. 447-455.

Tearney, G.J. et al., "Scanning single-mode fiber optic catheter-endoscope for optical coherence tomography," Optics Letters, Apr. 1, 1996, vol. 21, No. 7, pp. 543-545.

Zeis, Michael et al., "Color Business Report," ISSN 1055-3339. Jul. 2002, p. 5.

U.S. Appl. No. 12/487,481; filed Jun. 18, 2009; Stephen C. Jacobsen; office action dated Oct. 12, 2012.

U.S. Appl. No. 12/512,188; filed Jul. 30, 2009; Stephen C. Jacobsen; office action dated Nov. 19, 2012.

PCT Application PCT/US2010/051200; filed Oct. 1, 2010; Stephen C. Jacobsen; ISR mailed Jun. 3, 2011.

PCT Application PCT/US2010/051198; filed Oct. 1, 2010; Stephen C. Jacobsen; ISR mailed Jun. 3, 2011.

PCT Application PCT/US2010/051192; filed Oct. 1, 2010; Stephen C. Jacobsen; ISR mailed May 30, 2011.

Gaoping et al.; Research on the Measurement of Grin Lens Focused Spot Diameter and Resolution; Applied Optics; 1995; vol. 16, No. 6.

Obreja et al.; "Poly (vinyl-alcohol) Films for Microphotonics"; 2004, IEEE, pp. 1-4.

U.S. Appl. No. 13/940,791; filed Jul. 12, 2013; Stephen C. Jacobsen; office action dated Jun. 27, 2014.

U.S. Appl. No. 12/896,732; filed Oct. 1, 2010; Stephen C. Jacobsen; office action dated Mar. 13, 2014.

Subrahmanyam et al; Lens Aberrations; A Text Book of Optics; Jan. 1, 2004; Chapter 9, pp. 199-200; ; S. Chand & Co. Ltd.

Notice of Allowance for U.S. Appl. No. 13/940,791 dated Oct. 28, 2015, 12 pages.

Office Action for U.S. Appl. No. 13/966,030 dated Aug. 6, 2015, 28 pages.

Office Action for U.S. Appl. No. 14/248,184 dated Sep. 11, 2015, 19 pages.

Anonymous, "In vivo", http://web.archive.org/web/20070927001435/http:/en.wikipedia.org/wiki/In_vivo, as accessed on Jan. 1, 2016, 1 page.

Jung et al, "In Vivo Mammalian Brain Imaging Using One-and Two-Photon Fluorescence Microendoscopy", Journal of Neurophysiology, May 2004, vol. 92, pp. 3121-3133, American Physiological Society.

* cited by examiner

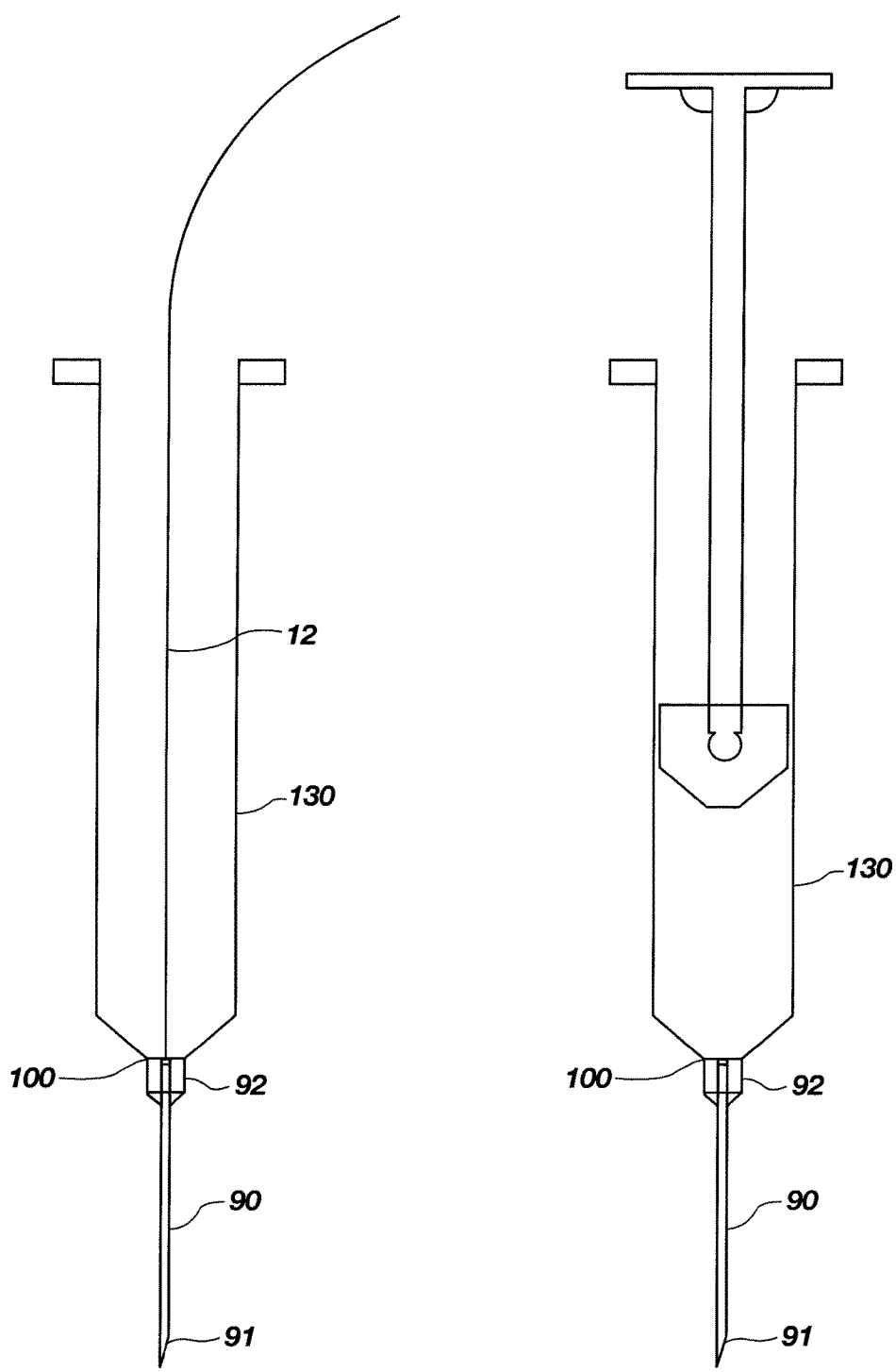
FIG. 8     FIG. 9

NEEDLE DELIVERED IMAGING DEVICE

CLAIM OF PRIORITY

The present application claims priority to U.S. Provisional Application No. 61/247,890 filed on Oct. 1, 2009 which is incorporated herein by reference in its entirety.

FIELD OF THE INVENTION

The present invention relates to medical devices, and more particularly to miniaturized in-situ imaging devices and methods of operation of said devices.

BACKGROUND

The present invention relates generally to imaging devices. More particularly, the present invention relates to small imaging devices that take advantage of advances in integrated circuit imaging technologies. Such small imaging devices can be particularly useful in medical diagnostic and treatment applications.

In minimally invasive surgery, a portal is formed in the patient's skin and tools are inserted into the body cavity to complete a procedure. For example, in laparoscopic surgery, a rigid laparoscope is passed through the portal providing direct visualization inside the body cavity, typically using fiber optics and some other imaging device. In comparison to the usual open surgery, there exist several advantages for the patient in minimally invasive procedures including: less pain, less strain of the body, faster recovery, smaller injuries (aesthetic reasons), and economic gain (shorter illness time). However, there exist some disadvantages for the medical practitioner when attempting to complete the procedure including: restricted vision, difficulty handling instruments, restricted mobility, difficult hand-eye coordination, and the lack of tactile perception. In many instances, multiple devices must typically be utilized to view the interior of a body cavity, move and/or dissect tissues and organs, and deliver medications, and/or aspirate fluids from the patient to effectuate a desired procedure.

SUMMARY OF THE INVENTION

It has been recognized that it would be advantageous to develop a method and apparatus for delivering a miniature imaging device into a portion of a patient through a needle, wherein the needle is capable of delivering fluids to and aspirating fluids from a patient. One embodiment of the present invention comprises a hollow elongated cylinder having a distal end and a proximal end, the proximal end configured to be removably connectable to a distal end of a syringe. An umbilical is removably inserted within the cylinder and configured for detachable connection to a data processor and a display device. The umbilical has an SSID disposed on its distal end. A lens system is disposed on a distal end of the SSID and the umbilical is inserted within the cylinder such that the distal end of the lens system is disposed at approximately the distal end of the cylinder.

In accordance with a more detailed aspect of the present invention, the system includes a lens system comprising a GRIN lens. In other aspect of the invention, the hollow elongated cylinder further comprises a valve disposed within the cylinder or at a proximal end of the cylinder. In one embodiment, the valve is a pressure-responsive slit valve. In another embodiment of the invention the hollow elongated cylinder comprises a coring or non-coring needle having a restraining device configured to secure the umbilical within the cylinder.

In another exemplary embodiment of the present invention, a medical imaging apparatus comprises a syringe having a hollow needle disposed on a distal end of the syringe. A lumen within the needle of the syringe defines a fluid communication path. The apparatus further comprises a pressure-responsive valve disposed within the fluid communication path and an umbilical removably inserted within the fluid communication path. In one aspect, the umbilical has an SSID disposed on a distal end thereof having a GRIN lens optically coupled thereto. The distal end of the umbilical is positioned within the fluid communication path such that the distal end of the GRIN lens is disposed at approximately the distal end of the fluid communication path.

In yet another embodiment of the present invention, the GRIN lens is directly bonded to the SSID wherein the distal end of the GRIN lens is shaped to approximate the shape of the distal end of the hollow needle.

In another aspect of the invention a method of real-time imaging tissue proximate to a distal end of a needle is disclosed comprising advancing a distal end of a needle within a portion of a patient, the needle having an imaging device removably inserted therein. The imaging device comprises an umbilical with an SSID disposed on a distal end thereof and a lens system optically coupled to the SSID. The umbilical is detachably connected to a data processor and a display device. The method further comprises transmitting image data from the imaging device to the data processor and the display device, positioning the distal end of the needle within the patient while viewing the anatomy of the patient on the display device, and thereafter removing the imaging device from the needle.

In another aspect of the invention, the method further comprises connecting the needle to a fluid source and injecting fluid into and/or aspirating a fluid from the patient.

In one embodiment of the present invention, a medical imaging apparatus comprises a hollow elongated cylinder having a distal end and a proximal end. The proximal end is configured to be removably connectable to a syringe. The apparatus further comprises an umbilical having a SSID disposed on a distal end thereof and a lens system disposed on a distal end of the SSID. The umbilical is mounted on an exterior portion of the hollow elongated cylinder and positioned such that a distal end of the lens system is near a distal end of the hollow elongated cylinder. In one aspect of the invention, the umbilical is removably mounted on an exterior portion of the hollow elongated cylinder. In another aspect, the umbilical is permanently mounted to an exterior portion of the hollow elongated cylinder.

BRIEF DESCRIPTION OF THE DRAWINGS

The present invention will become more fully apparent from the following description and appended claims, taken in conjunction with the accompanying drawings. Understanding that these drawings merely depict exemplary embodiments of the present invention they are, therefore, not to be considered limiting of its scope. It will be readily appreciated that the components of the present invention, as generally described and illustrated in the figures herein, could be arranged and designed in a wide variety of different configurations. Nonetheless, the invention will be described and explained with additional specificity and detail through the use of the accompanying drawings in which:

FIG. 8 is a side view of a syringe connected to the needle of FIG. 4;

FIG. 9 is a side view of the syringe of FIG. 8 with the imaging device removed;

Figure 1:
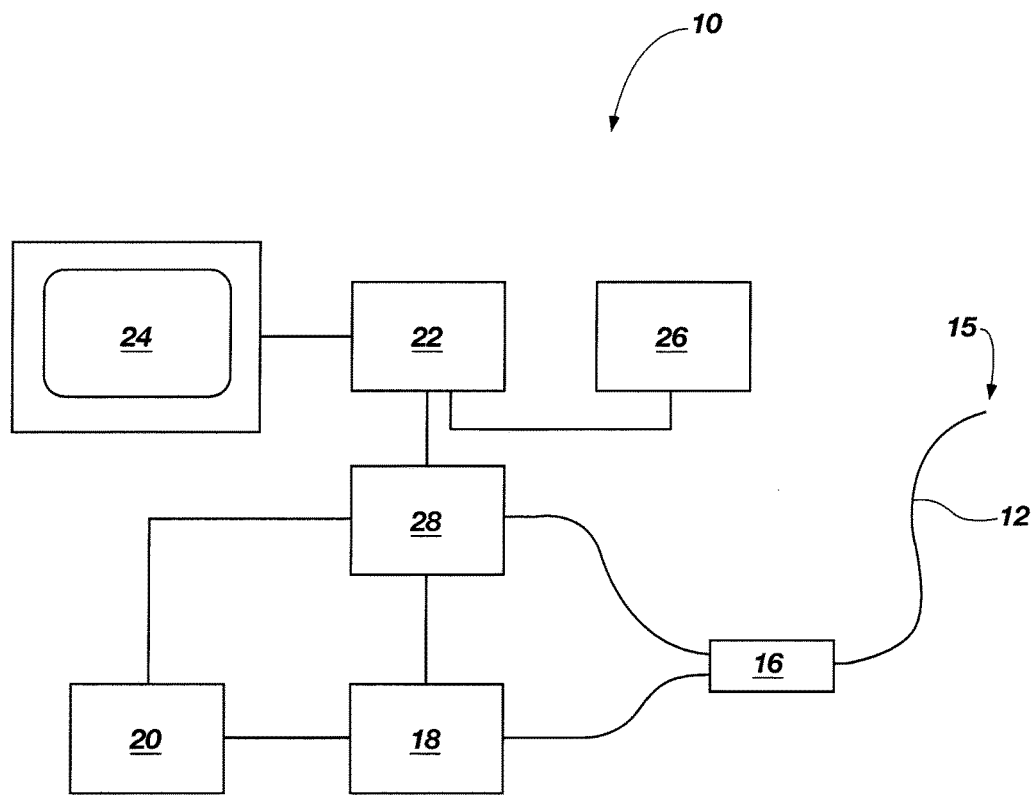
FIG. 1 is a view of a medical imaging system according to one embodiment of the present invention.

Reference will now be made to the exemplary embodiments illustrated, and specific language will be used herein to describe the same. It will nevertheless be understood that no limitation of the scope of the invention is thereby intended.

DETAILED DESCRIPTION OF EXAMPLE EMBODIMENT(S)

The following detailed description of exemplary embodiments of the invention makes reference to the accompanying drawings, which form a part hereof and in which are shown, by way of illustration, exemplary embodiments in which the invention may be practiced. While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

The following detailed description and exemplary embodiments of the invention will be best understood by reference to the accompanying drawings, wherein the elements and features of the invention are designated by numerals throughout.

It must be noted that, as used in this specification and the appended claims, singular forms of "a," "an," and "the" include plural referents unless the context clearly dictates otherwise.

An "SSID," "solid state imaging device," "SSID chip," or "solid state imaging chip" in the exemplary embodiments generally comprises an imaging array or pixel array for gathering image data. In one embodiment, the SSID can comprise a silicon or other semiconductor substrate or amorphous silicon thin film transistors (TFT) having features typically manufactured therein. Features can include the imaging array, conductive pads, metal traces, circuitry, etc. Other integrated circuit components can also be present for desired applications. However, it is not required that all of these components be present, as long as there is a means of gathering visual or photon data, and a means of sending that data to provide a visual image or image reconstruction.

The term "umbilical" can include the collection of utilities that operate the SSID or the micro-camera as a whole. An umbilical includes a conductive line, such as electrical wire(s) or other conductors, for providing power, ground, clock signal, and output signal with respect to the SSID, though not all of these are strictly required. For example, ground can be provided by another means than through an electrical wire (e.g., to a camera housing such as micromachined tubing). The umbilical can also include other utilities such as a light source, temperature sensors, force sensors, fluid irrigation or aspiration members, pressure sensors, fiber optics, microforceps, material retrieval tools, drug delivery devices, radiation emitting devices, laser diodes, electric cauterizers, and electric stimulators, for example. Other utilities will also be apparent to those skilled in the art and are thus comprehended by this disclosure.

"GRIN lens" or "graduated refractive index lens" refers to a specialized lens that has a refractive index that is varied radially from a center optical axis to the outer diameter of the lens. In one embodiment, such a lens can be configured in a cylindrical shape, with the optical axis extending from a first flat end to a second flat end. Thus, because of the differing refractive index in a radial direction from the optical axis, a lens of this shape can simulate the effects of a more traditionally shaped lens. The GRIN lens may be a GRIN rod lens or any other GRIN lens configuration.

In minimally invasive surgery, a portal is formed in the patient's skin and tools are inserted into the body cavity. For example, in laparoscopic surgery, a rigid laparoscope is passed through the portal created in the patient's skin providing direct visualization inside the body cavity. While the surgeon may have a limited view of the body cavity, a separate device must typically be utilized to deliver medications and/or remove tissues. Advantageously, the present invention allows a medical practitioner to position a needle while simultaneously viewing the area adjacent the tip of the needle without introducing any additional viewing devices other than the device immediately associated with the needle itself. The device also advantageously allows the medical practitioner to strategically deliver fluids and/or aspirate fluids from a patient through a portal no larger than the desired needle diameter (e.g., no greater than 1 millimeter).

Figure 2:
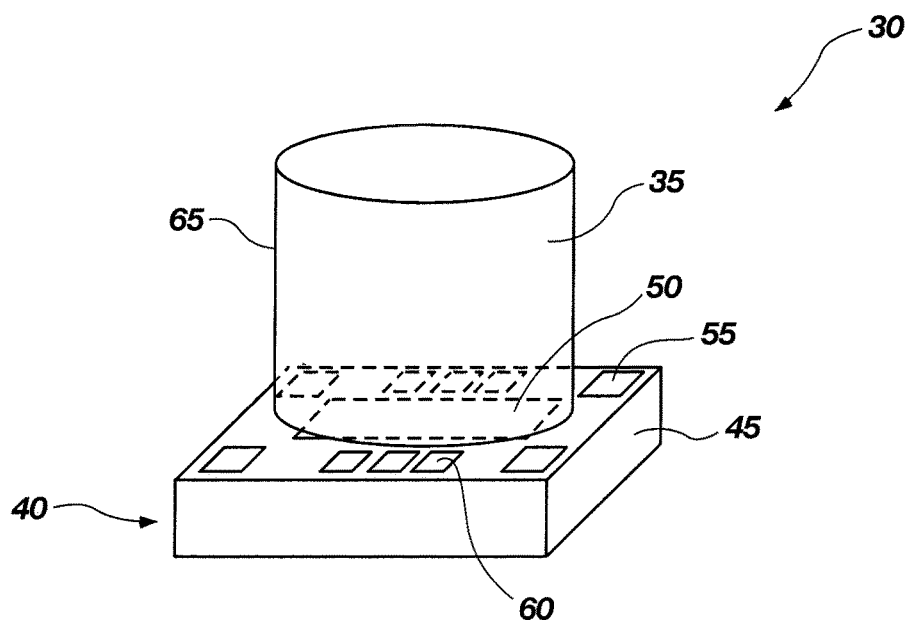
FIG. 2 is a perspective view of an imaging device according to one embodiment of the present invention.
Figure 3:
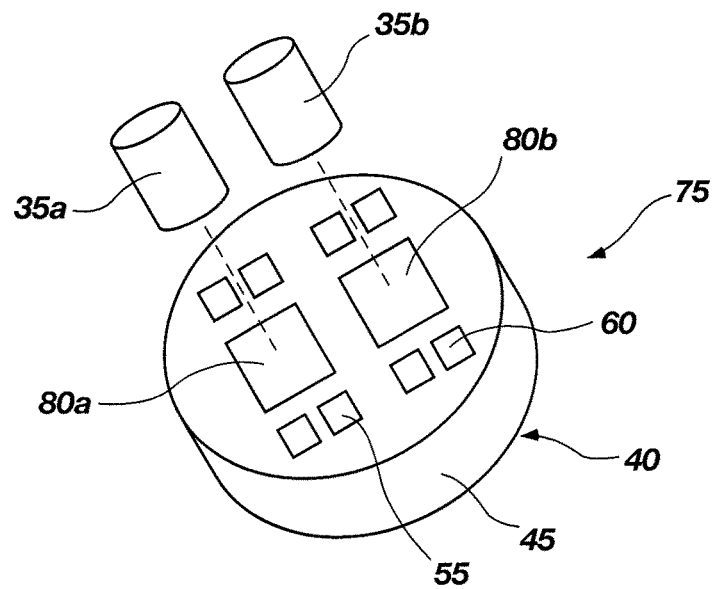
FIG. 3 is perspective view of an imaging device according to one embodiment of the present invention.
Figure 4:
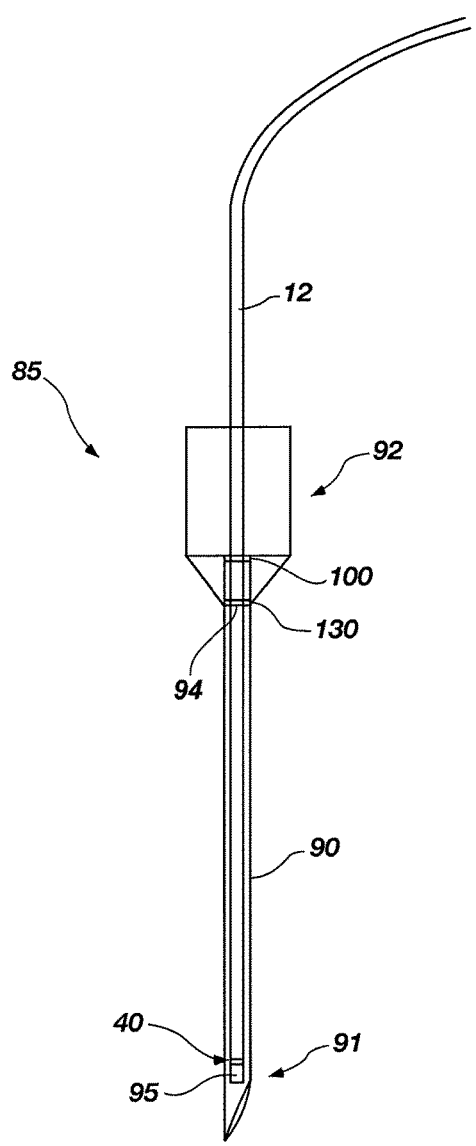
FIG. 4 is a side view of a needle having an imaging device disposed therein according one embodiment of the present invention.
Figure 5:
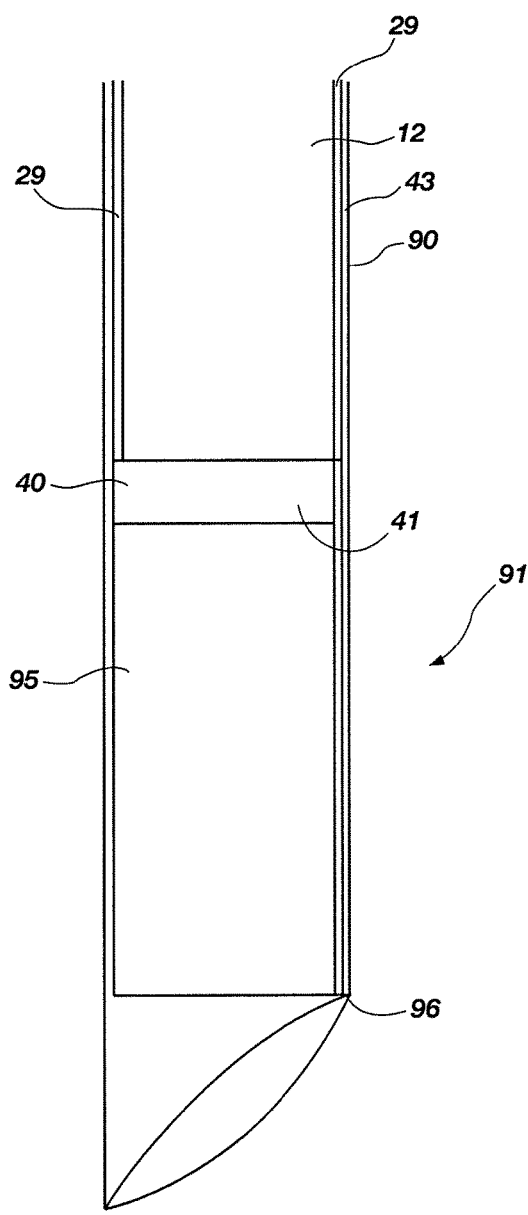
FIG. 5 is a blown up view of the distal end of the needle of FIG. 4.
Figure 6:
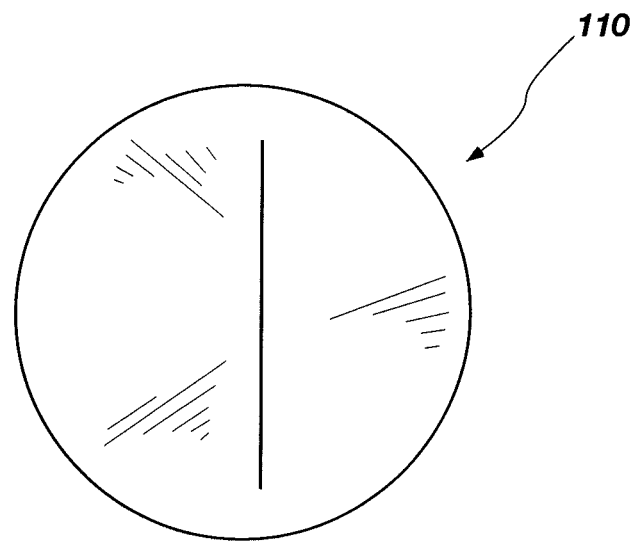
FIG. 6 is a top view of a slit-valve according to one embodiment of the present invention.
Figure 7:
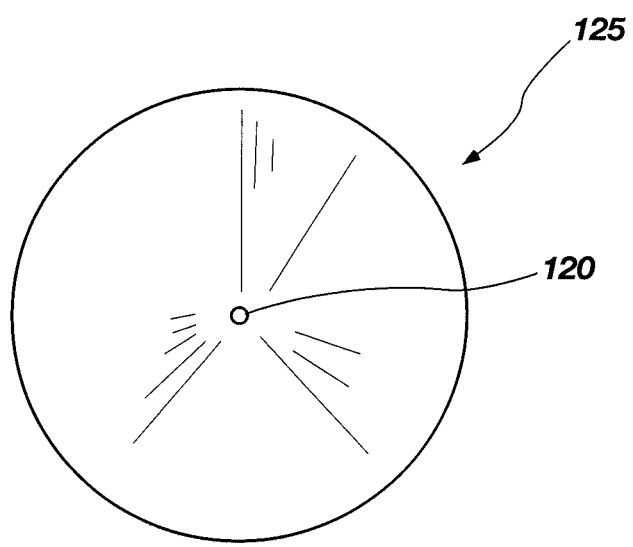
FIG. 7 is a top view of an orifice valve according to one embodiment of the present invention.

With reference to FIGS. 1 through 3, in one embodiment of the present invention, a medical imaging system 10 comprises an umbilical 12 having an imaging device disposed at a distal tip 15 of the umbilical 12. A processor 22, such as an appropriately programmed computer, is provided to control the imaging system 10 and create an image of anatomy adjacent the distal tip portion 15, within a patient (not shown), displayable on a monitor 24, and storable in a data storage device 26. An interface 28 is provided which supplies power to the imaging device and feeds a digital image signal to the processor based on a signal received from the imaging device via conductive wires 29 through the umbilical 12. A light source 60 may also be provided at the distal end of the umbilical 12. In one aspect, the system further includes a fitting 16 enabling an imaging fluid, such as a clear saline solution, to be dispensed to the distal tip portion of the umbilical 12 from a reservoir 18 through an elongated tubular member (not shown) removably attached to the umbilical 12 to displace body fluids as needed to provide a clearer image. A pump 20 is provided, and is manually actuated by a medical practitioner performing a medical imaging procedure, or can be automated and electronically controlled so as to dispense fluid on demand according to control signals from the practitioner, sensors, or according to software commands.

Referring now to FIG. 2, an imaging device, indicated generally at 30, includes a GRIN lens 35 and an SSID 40. The SSID 45 can comprise a silicon or other semiconductor substrate or amorphous silicon thin film transistors (TFT) 45 having features typically manufactured therein. Features including the imaging array 50, the conductive pads 55, metal traces (not shown), and circuitry (not shown) can be fabricated therein. With respect to the conductive pads, the connection between conductive pads and a conductive line of an umbilical (not shown) can be through soldering, wire bonding, solder bumping, eutectic bonding, electroplating, and conductive epoxy. However, a direct solder joint having no wire bonding between the electrical umbilical and the conductive pads is also contemplated herein. In one embodiment, the conductive line of the umbilical provides power, ground, clock signal, and output signal with respect to the SSID 40. Other integrated circuit components can also be present for desired applications, such as light emitting diodes (LEDs) 60, for providing light to areas around the GRIN lens 35. It is not required that all of these components be present, as long as there is a visual data gathering and sending image device present, and some means provided to connect the data gathering and sending device to a visual data signal processor. Other components, such as the umbilical, housing, adaptors, utility guides, and the like, can also be present, though they are not shown in FIG. 2. The SSID 40 can be any solid state imaging device, such as a CCD, a CID, or a CMOS imaging device. Also shown, the GRIN lens 35 is coated with an opaque coating 65 on the curved surface to prevent light from entering the lens at other than the flat surface that is most distal with respect to the SSID 40. Additional principles of operation and details of construction of similar imaging device assemblies can be found in U.S. patent application Ser. Nos. 10/391,489, 10/391,490, 11/292,902, and 10/391,513 each of which are incorporated herein by reference in their entireties.

Referring now to FIG. 3, in one embodiment of the present invention, an imaging device is shown generally at 75 which can provide stereoscopic imaging. Specifically, multiple imaging arrays 80*a*, 80*b*, are shown on a common SSID 40 in a coplanar arrangement. A pair of GRIN lenses 35*a*, 35*b* are shown as they would be optically coupled to imaging arrays 80*a*, 80*b*, respectively. Other than the imaging array, other features are also present in the SSID 40, including conductive pads 55 for providing an electrical connection to an umbilical (not shown).

With specific reference to FIGS. 1 through 5, in one embodiment of the present invention, a medical apparatus shown generally at 85 is provided comprising a needle 90 having a distal end 91 and a proximal end 92. The proximal end 92 of the needle 90 is configured to be removably connectable to a distal end of a syringe 130 (shown generally in FIG. 8). The apparatus 85 further comprises an umbilical 12 removably inserted within the needle 90 and configured for detachable connection to a data processor 22 and a display device 24. The apparatus 85 further comprises an SSID 40 disposed on a distal end 15 of the umbilical 12 and a lens system 95 disposed on a distal end 41 of the SSID 40. The umbilical 12 is inserted within the needle 90 such that the distal end 96 of the lens system 95 is disposed at approximately the distal end 91 of the needle 90. In one aspect of the invention, the umbilical 12 comprises conductive wires 42 for providing energy to the SSID 40 and/or for transmitting image data from the SSID 40 to the data processor 22. In another aspect of the invention, the umbilical further comprises a light source 43 for illuminating interior portions of the anatomy of the patient. In one aspect of the present invention, the lens system 95 is a single GRIN lens bonded directly to the SSID 40.

In another embodiment of the invention, the distal end 96 of the lens system 95 is shaped to approximate the shape of the distal end 91 of the needle 90. Advantageously, the distal end 96 of the lens system 95 can be positioned flush with the distal end 91 of the needle 90 but in such a manner that the lens system 95 does not increase patient discomfort by changing the shape of the distal end 91 of needle 90. In one aspect of the invention, the lens system 95 substantially occludes the needle 90. In another aspect, positioning the lens system 95 flush with the distal end 91 of the needle 90 advantageously minimizes image aberration. In yet another aspect, the distal end 91 of the needle 90 is translucent thereby allowing for imaging outside the perimeter of the needle 90.

With reference now to FIGS. 4 through 7, in another embodiment of the present invention, the medical apparatus 85 further comprises a pressure responsive two-way valve member 100 disposed within the lumen of the needle 90. As the umbilical 12 is removed from the needle, the valve member 100 advantageously minimizes back flow of fluids from the patient back through the needle when the valve member is under pressures normally exerted by fluids in the patient. The valve member 100 is configured such that it allows fluids to be injected through the needle and into the patient upon positive pressure injection from a syringe or other injection device and/or remove fluids from a patient upon negative pressure from a syringe or other fluid removal device. In one aspect of the invention, the pressure responsive two-way valve member 100 is a slit-valve 110. In yet another aspect of the invention, the two-way pressure responsive valve member 100 is an orifice valve 120 disposed in a diaphragm. The valve member 100 is typically biased in a closed position. The diaphragm and/or slit-valve may comprise any polymeric, thermoplastic and/or elastomeric material suitable for preventing backflow of fluids from the body yet opening in a distal and proximal direction to a pre-determined pressure value.

In yet another embodiment, the needle 90 further comprises a securement device 94 for removably securing the umbilical 12 at a desired position within the needle 90. The securement device can be a miniature compression fitting or any other device suitable for securing the umbilical 12 in place.

Figure 11:
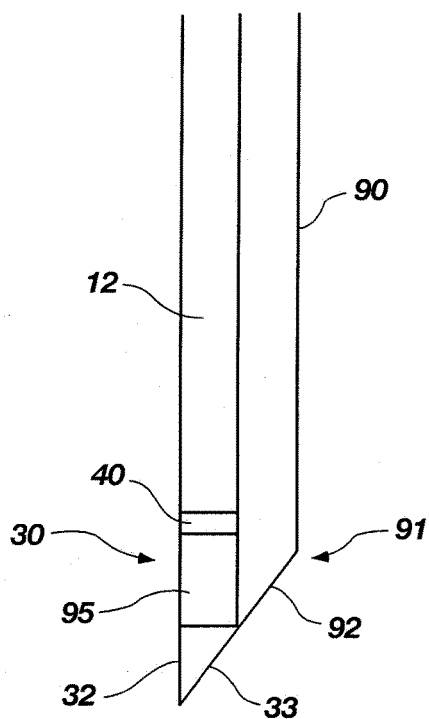
FIG. 11 is a close up view of an imaging device disposed on an exterior of a needle.
Figure 10:
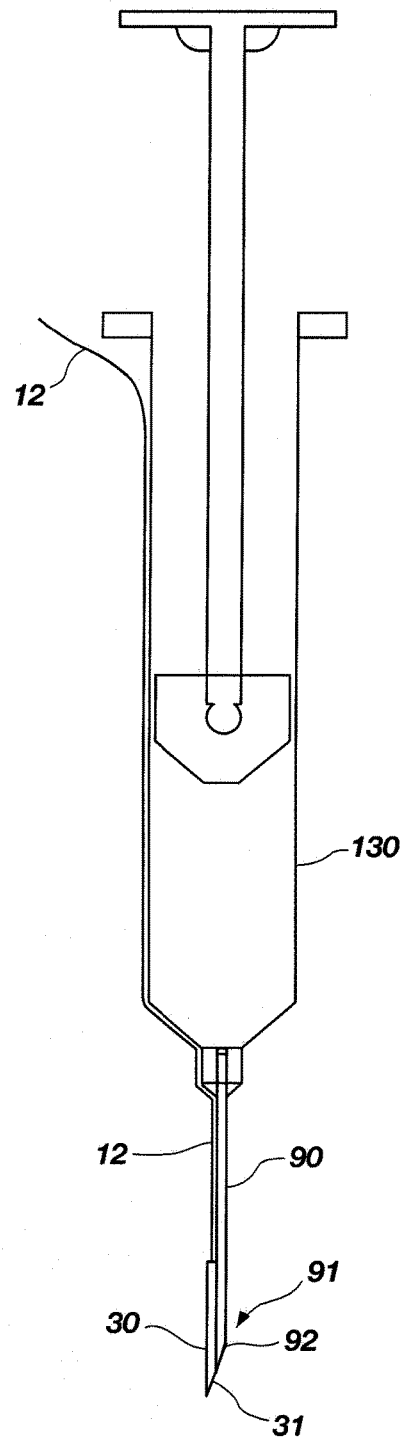
FIG. 10 is a side view of one embodiment of the present invention with an imaging device disposed on an exterior of a needle.

Referring now to FIGS. 10 and 11, in another embodiment, the imaging device 30 may be removably secured on the exterior of needle 90. In yet another embodiment, the imaging device 30 may be permanently attached to the exterior of the needle 90. Advantageously, while secured to an exterior of the needle 90, the imaging device 30 would not need to be removed from the needle in order to inject or aspirate fluids to or from the patient. In one embodiment where the umbilical 12 and imaging device 30 are positioned on an exterior of the needle 90, a distal end of the imaging device 30 is shaped to approximate the shape of the distal end of the needle 90 and positioned on the distal end 91 of the needle 90 such that the face 31 of the imaging device 30 is coplanar (i.e., oriented at the same angle) with the face 92 of the needle 90. In this manner, the penetration of the imaging device 30 and needle 90 into the patient is accomplished without undue discomfort to the patient. In another embodiment, the imaging device 30 is equipped with a piercing member 32 to facilitate penetration into the patient as noted above. The face 33 of piercing member 32 is oriented to match the pitch and orientation of the face 92 of needle 90. In one embodiment of the invention, the piercing member 32 is translucent so as to permit viewing outside the perimeter of the piercing member 32.

In one aspect of the invention, the umbilical 12 of imaging device 30 is tethered to a data processor which is disposed on a proximal portion of needle 90 or on a syringe. The data processor is capable of powering the imaging device 30 as well as receiving and transmitting image data from the imaging device 30 to a remote system, including a display. In this manner, the imaging device 30 is not tethered to a remote system by the umbilical 12 but retains the ability to receive and transmit image data.

Referring now to FIGS. 1, 4, 5, 8, and 9, in another embodiment of the present invention, a method of real-time imaging tissue proximate to a distal end 91 of a needle 90 is disclosed comprising advancing a distal end 91 of a needle 90 within a portion of a patient. The needle 90 has an imaging device 30 removably inserted therein comprising an umbilical 12 with an SSID 40 disposed on a distal end of the umbilical 12 and a lens system 95 optically coupled to the SSID 40. The umbilical 12 is detachably connected to a data processor 22 and a display device 24. The method further comprises transmitting image data from the imaging device 30 to the data processor 22 and the display device 24, positioning the distal end 91 of the needle 90 within the patient while viewing the anatomy of the patient on the display device 24, and removing the imaging device 30 from the needle 90. In one embodiment, the method further comprises connecting the needle 90 to a fluid source 16 and injecting a fluid into the patient after removing the imaging device 30 from the needle 90. The method further comprises connecting a syringe 130 to the needle 90 and aspirating fluid from the patient.

With reference to FIGS. 10 and 11, in another embodiment of the present invention, a method of real-time imaging tissue proximate to a distal end 91 of a needle 90 is disclosed comprising advancing a distal end 91 of a needle 90 within a portion of a patient. The needle 90 has an imaging device 30 disposed on an exterior of the needle comprising an umbilical 12 with an SSID 40 disposed on a distal end of the umbilical 12 and a lens system 95 optically coupled to the SSID 40. The umbilical 12 is detachably connected to a data processor 22 and a display device 24. The method further comprises transmitting image data from the imaging device 30 to the data processor 22 and the display device 24, positioning the distal end 91 of the needle 90 within the patient while viewing the anatomy of the patient on the display device 24. In one embodiment, the method further comprises connecting the needle 90 to a fluid source 16 and injecting a fluid into the patient. The method further comprises connecting a syringe 130 to the needle 90 and aspirating fluid from the patient.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. A medical imaging apparatus, comprising:
   a syringe having a hollow needle fixed on a distal end of the syringe, a distal end of the syringe and a lumen of the hollow needle being collinear and defining a fluid communication path from the apparatus to a patient;
   a valve disposed within the fluid communication path;
   an umbilical removably inserted within the fluid communication path and extending into the syringe, the umbilical having a solid state imaging chip disposed on a distal end thereof, the umbilical configured to power the solid state imaging chip and to be removed prior to injection of fluids into and aspiration of fluids out of the patient through the fluid communication path; and
   a lens optically coupled to the solid state imaging chip, wherein the distal end of the umbilical is positioned within the fluid communication path such that the distal end of the lens is removably disposed at approximately the distal end of the fluid communication path, wherein the distal end of the lens substantially occludes the fluid communication path during placement of the medical apparatus within the patient.

2. The medical imaging apparatus of claim 1, wherein a GRIN lens is directly bonded to the solid state imaging chip.

3. The medical imaging apparatus of claim 1, wherein the valve is a pressure-responsive slit-valve.

4. The medical imaging apparatus of claim 1, wherein the valve is a pressure-responsive orifice valve.

5. The medical imaging apparatus of claim 2, wherein the distal end of the hollow needle comprises a face having a slope and wherein the lens system is shaped to approximate the shape of the distal end of the needle.

6. A medical imaging apparatus, comprising:
   a syringe having a hollow needle fixed on a distal end of the syringe, an interior of the syringe and a lumen of the hollow needle defining a fluid communication path to a patient;
   a valve disposed within the fluid communication path;
   an umbilical removably inserted within the fluid communication path of the lumen of the hollow needle and extending through a front of the syringe and out a back of the syringe, the umbilical having a solid state imaging chip disposed on a distal end thereof, the umbilical further configured to provide power to the solid state imaging chip and to be removed prior to injection of fluids into or aspiration of fluids out of the patient through the fluid communication path; and
   a lens optically coupled to the solid state imaging chip, wherein the distal end of the umbilical is removably positioned within the fluid communication path such that the distal end of the lens is disposed within the distal end of the fluid communication path and wherein the distal end of the umbilical occludes substantially all of an internal diameter of the hollow needle during placement of the needle within the patient.

7. The medical imaging apparatus of claim 6, wherein then the lens occludes substantially all of an internal diameter of the lumen of the hollow needle.

8. The medical imaging apparatus of claim 6, wherein the valve is an orifice valve disposed substantially within the lumen of the hollow needle.

9. The medical imaging apparatus of claim 6, wherein the valve is an orifice valve disposed substantially within the interior of the syringe.

10. The medical imaging apparatus of claim 6, wherein the hollow needle is a non-coring needle.

11. The medical imaging apparatus of claim 6, wherein the hollow needle is a coring needle.

12. The medical imaging apparatus of claim 7, wherein the slope of a distal end of the lens is shaped to approximate the slope of the distal end of the needle, wherein the slope of the distal end of the needle is greater than zero.

13. The medical imaging apparatus of claim 7, further comprising a securement device for removably securing the umbilical at a desired position within the needle.

14. A medical imaging apparatus, comprising:
   a syringe having a hollow needle fixed on a distal end of the syringe, an interior of the syringe and a lumen of the hollow needle defining a fluid communication path to a patient;
   an umbilical removably inserted within the fluid communication path of the lumen of the hollow needle and extending into the syringe, the umbilical having a solid state imaging chip disposed on a distal end thereof, the umbilical further configured to provide power to the solid state imaging chip and to be removed prior to injection of fluids into or aspiration of fluids out of the patient through the fluid communication path; and
   a lens optically coupled to the solid state imaging chip, wherein the distal end of the umbilical is positioned within the fluid communication path such that the distal end of the lens is disposed at approximately the distal end of the fluid communication path and wherein the lens occludes substantially all of an internal diameter of the distal end of the hollow needle.

15. The apparatus of claim 14, wherein a distal end of the needle is translucent.

16. The apparatus of claim 14, wherein a distal end of the lens is flush with a distal end of the needle.

17. The apparatus of claim 14, wherein the distal end of the lens is shaped to approximate the shape of the distal end of the needle.

* * * * *